United States Patent [19]

Hackl et al.

[11] Patent Number: 5,124,451
[45] Date of Patent: Jun. 23, 1992

[54] PROCESS FOR THE N-ALKYLATION OR UREAS

[75] Inventors: Kurt A. Hackl; Heinz Falk, both of Linz, Austria

[73] Assignee: Chemie Linz Gesellschaft m.b.H., Linz, Austria

[21] Appl. No.: 728,130

[22] Filed: Jul. 10, 1991

[30] Foreign Application Priority Data

Aug. 14, 1990 [AT] Austria ................................ 1691/90

[51] Int. Cl.$^5$ ................ C07D 275/06; C07D 295/215
[52] U.S. Cl. .................................... 544/169; 546/226; 548/538; 564/56; 564/57; 564/61
[58] Field of Search ......................... 544/169; 546/226; 548/538; 564/56, 57, 61

[56] References Cited

PUBLICATIONS

Sidgwick, *The Organic Chemistry of Nitrogen*, (1966), 3rd ed., pp. 428, 429.

*Primary Examiner*—Robert W. Ramsuer
*Attorney, Agent, or Firm*—Wenderoth, Lind & Ponack

[57] ABSTRACT

Process for the N-alkylation of ureas by reacting a urea with an alkylating agent in the presence of a solid base and a phase transfer catalyst in a diluent.

10 Claims, No Drawings

PROCESS FOR THE N-ALKYLATION OR UREAS

The invention relates to a process for the preparation of N-alkylated ureas by reacting a urea with an alkylating agent.

Hitherto, it has been necessary to prepare N-alkylated ureas by indirect routes, namely, for example, via the preparation of an amine, which had to be substituted correspondingly to the desired urea, and which was then reacted with the urea by exchange of an amine moiety of the urea or was reacted with an appropriate isocyanate or carbamoyl chloride. A direct N-alkylation of ureas with alkylating agents has hitherto been considered impossible.

Thus it is described in R. A. Jacobson, J.Am.Chem.-Soc. 58, 1984 (1936) that the attempt to alkylate ureas on the nitrogen atom by reacting monosodium ureas with alkyl halides did not proceed successfully. It is evident from P. A. Ongley, Trans.Proc.Roy. Soc., New Zealand 77, 10 (1948) that alkylisoureas and not N-alkylated ureas are formed when urea is alkylated with alkyl sulfates. These results are confirmed in F. Korte: Methodicum Chimicum, Volume 6, 716 and 732, Georg Thieme Verlag, Stuttgart, 1974. It is described therein that ureas are always alkylated on the oxygen atom and not on the nitrogen atom when reacted with alkyl halides, and that isoureas are formed when ureas are alkylated with dialkyl sulfates or esters of p-toluene sulfonic acid.

U. Peterson and E. Kühle in E. Müller: Methoden der Organischen Chemie ("Methods of Organic Chemistry") Houben-Weyl; 4th edition, volume E4, 335 et seq and 594, Georg Thieme Verlag Stuttgart—New York, 1983 and the literature quoted therein also confirm that only O-alkylation of ureas is possible.

It has now been found, unexpectedly, that ureas can, however, be alkylated on the nitrogen atom if the urea is reacted with an alkylating agent in the presence of a phase transfer catalyst and a base.

The invention therefore relates to a process for the preparation of ureas of the formula

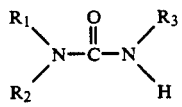  I in which $R_1$ and $R_2$ independently of one another denote hydrogen, a linear, branched or cyclic alkyl group which is unsubstituted or substituted by groups inert under the conditions of the reaction, or an aralkyl group, or $R_1$ and $R_2$, together with the nitrogen atom, denote a non-aromatic, heterocyclic ring and $R_3$ denotes an alkyl group which is unsubstituted or substituted by groups inert under the conditions of the reaction, the tertiary butyl group being excluded, characterized in that a urea of the formula

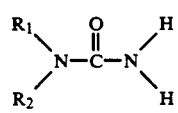  II in which $R_1$ and $R_2$ have the abovementioned meaning is N-alkylated in the presence of a solid base and in the presence of a phase transfer catalyst in a diluent at temperatures of 0 to 150° C. with an alkylating agent of the formula

  III in which $R_3$ has the meaning indicated above and n denotes the numbers 1 or 2, X representing a halide or a sulfonic acid or bisulfate group in the event that n denotes the number 1, and X representing a sulfate group in the event that n denotes the number 2.

The urea employed has the formula

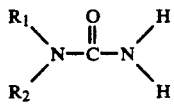  II wherein $R_1$ and $R_2$ independently of one another denote hydrogen, a linear, branched or cyclic alkyl group which is unsubstituted or substituted by groups inert under the conditions of the reaction, or an aralkyl group, or $R_1$ and $R_2$, together with the nitrogen atom, denote a non-aromatic heterocyclic ring.

Alkyl groups are to be understood here as meaning alkyl groups having 1 to 22, preferably 2 to 18, C atoms, such as, for example, ethyl, propyl, isopropyl, tert.-butyl, isopentyl, methylcyclopentyl, cyclohexyl, 3-ethylhexyl, octyl, decyl, dodecyl, hexadecyl or octadecyl groups.

The alkyl groups can be unsubstituted or substituted by groups inert under the conditions of the reaction, such as, for instance, fluorine atoms, nitro groups, alkenyl, alkylidene or aryl groups or alkoxy groups having 1 to 5 C atoms, for example methoxy, ethoxy, isopropoxy, butoxy or phenoxy groups. The alkyl groups are preferably unsubstituted.

Aralkyl groups are to be understood as meaning benzyl or phenylethyl groups, it being possible for the phenyl groups to be substituted by groups inert under the conditions of the reaction, such as alkyl groups having 1 to 5 C atoms, for example ethyl, isopropyl or isopentyl groups, alkoxy groups having 1 to 5 C atoms, for example methoxy, ethoxy, isopropoxy or butoxy groups, halides, such as fluorine, chlorine or bromine, or nitro groups. $R_1$ and $R_2$, together with the nitrogen atom, can also form a non-aromatic, heterocyclic ring, that is to say, for example, a pyrrolidine, piperidine, morpholine or 1,4-thiazane ring.

$R_1$ and $R_2$ independently of one another preferably denote hydrogen or an unsubstituted, linear or branched alkyl group having 2 to 10 C atoms, or $R_1$ and $R_2$, together with the nitrogen atom, denote a non-aromatic, heterocyclic ring, preferably the pyrrolidine or morpholine ring.

Compounds of the formula II can either by prepared by means of the process according to the invention or they can be prepared by one of the customary, known processes, for instance by reacting urea or isocyanic acid with a suitable amine.

Suitable bases are solid bases, such as alkali metal hydroxides, for example potassium hydroxide or sodium hydroxide, or alkali metal amides, for example sodium amide or potassium amide. It is preferable to employ alkali metal hydroxides, and it is advantageous if the alkali metal hydroxide has a small content of a carbonate, such as potassium carbonate or sodium carbonate, amounting to 2 to 20 mol %, relative to the alkali metal hydroxide. The base is used in excess in a solid, powdered form or in the form of pellets. It is preferable to use 1.5 to 8 mol, particularly preferably 3 to 5 mol, of the solid base per mole of urea of the formula II.

Suitable catalysts are customary phase transfer catalysts or dimethyl sulfoxide. A summary of phase transfer catalysts which can be used and their possible used in various diluents is disclosed in W. E. Keller: Phase transfer reactions (Fluka Compendium), volumes 1 and 2; Georg Thieme Verlag Stuttgart—New York, 1986 and 1987. It is preferable to employ quaternary ammonium salts, such as, for example, tetrabutylammonium bisulfate, tetrabutylammonium chloride or benzyltriethylammonium chloride, as the phase transfer catalysts. If urea itself is used as the urea of the formula II, dimethyl sulfoxide is used as the catalyst. The choice of the catalyst in a particular case is made on the basis of the particular diluent used or the particular starting material used. The alkylating agent employed is a compound of the formula

$(R_3)_n-X$  III in which $R_3$ denotes an alkyl group which is unsubstituted or substituted by groups inert under the conditions of the reaction, the tert.-butyl group being excluded, and n denotes the number 1 or 2, X representing a halide or a sulfonic acid or bisulfate group in the event that n denotes the number 1, and X representing a sulfate group in the event that n denotes the number 2. A halide is to be understood here as meaning chloride, bromide or iodide. X in the formula III preferably denotes a halide, a sulfonic acid group or a sulfate group. Alkyl groups are to be understood as meaning the alkyl groups mentioned above, which can be unsubstituted or substituted by groups inert under the conditions of the reaction, such as are mentioned above, the tert.-butyl group being excluded. The alkylating agent is generally employed in an equimolar ratio to the urea of the formula II, it being possible, however, to use an excess of one or other of the reactants in an individual case.

The diluents employed are diluents which are inert under the conditions of the reaction and which are solvents for the urea of the formula II and the alkylating agent. These are aromatic hydrocarbons, for example benzene, toluene or xylene, higher aliphatic hydrocarbons, for example paraffins, aromatic halogenated hydrocarbons, for example chlorobenzene or trichlorobenzens, ethers, for example tetrahydrofuran, or dimethyl sulfoxide or mixtures of such diluents. It is preferable to employ aromatic hydrocarbons or dimethyl sulfoxide, particularly preferably toluene or dimethyl sulfoxide. If dimethyl sulfoxide is used as the diluent, it also acts at the same time as the catalyst. The base employed should not be completely soluble in the diluent used. If the starting material of the formula II is urea, dimethyl sulfoxide is used as the diluent.

The process according to the invention is carried out by initially taking the urea of the formula II, dissolved in the diluent. It is preferable for the diluent to have been dried before use. The solid base is then added in the form of pellets or in a powdered form and is thoroughly suspended by vigorous stirring, after which the catalyst and the alkylating agent are added. It has been found that, if dimethyl sulfoxide is used as the catalyst and diluent, it can be advantageous first to suspend the pelletized or powdered solid base thoroughly in dimethyl sulfoxide and then to stir in the urea of the formula II and the alkylating agent, it being preferable in this case to employ an alkyl halide as the alkylating agent.

The reaction mixture is vigorously stirred and, if appropriate, heated to temperatures up to 150° C. It is preferably heated to 70° to 150° C., particularly preferably to the reflux temperature of the particular diluent used. In the event that dimethyl sulfoxide is used as the catalyst and diluent, the reaction mixture is not heated to reflux temperature; in this case a temperature of 0° to 100° C., preferably 20° to 70° C., is used.

The urea of the formula I is formed in the course of the reaction.

When the reaction is complete, water is added and the urea of the formula I is extracted from the reaction mixture by means of an extraction agent. The extraction agents employed are water-immiscible, organic extraction agents, such as halogenated hydrocarbons, for example methylene chloride or chloroform, or ethers, for example diethyl ether or diisopropyl ether. The organic phase is washed with water and dried, and the diluent is evaporated off, it being possible for a subsequent drying in vacuo to be carried out. In general, the purity of the urea of the formula I prepared in this manner is adequate. If necessary, a purification stage, for example by recrystallization, chromatography or distillation, can also follow.

In a preferred embodiment, ethyl-, isopropyl-, butyl-, tert.-butyl- or decyl-urea or pyrrolidine carboxamide or morpholine carboxamide is dissolved in toluene, 3 to 5 equivalents of potassium hydroxide or sodium hydroxide pellets containing 4 to 10 mol % of potassium carbonate or sodium carbonate are added with vigorous stirring, together with 0.04 to 0.06 equivalent of a quaternary ammonium salt as phase transfer catalyst, and the mixture is heated at reflux temperature. When the reaction is complete, water is added to the reaction mixture and it is extracted several times with methylene chloride and/or chloroform. The combined organic phases are washed with water and dried, and the diluent is evaporated off, after which the product is subsequently dried in vacuo.

In another preferred embodiment, 3 to 5 equivalents of powdered potassium hydroxide are suspended in dimethyl sulfoxide, and one equivalent of urea and one equivalent or alkyl halide are added. The reaction mixture is stirred at temperatures from 20° to 70° C., water is added when the reaction is complete, and the mixture is extracted with methylene chloride and/or chloroform. The combined organic phases are dried and the diluent is evaporated off, after which a further drying is carried out under an oil pump vacuum.

Alkylated ureas are prepared in the manner described in good yields and in a good state of purity without indirect routes. The process thus constitutes an enrichment of the art.

EXAMPLE 1

2.32 g of N-butylurea (20 mmol), 3.2 g of NaOH pellets (80 mmol), 0.55 of potassium carbonate (4 mmol) and 280 mg (1 mmol) of tetrabutylammonium chloride were suspended in 40 ml of toluene, and 2.18 g of ethyl bromide (20 mmol) were added with vigorous stirring. The reaction mixture was heated at reflux temperature for 2 hours, 150 ml of distilled water were added, and the mixture was extracted with 50 ml of chloroform and 50 ml of methylene chloride. The combined organic phases were washed with water, dried over sodium sulfate and evaporated. The residue was dried further in vacuo. This gave 2.16 g of N-butyl-N'-ethylurea, i.e. 76% of theory. $^1$H-NMR (CDCl$_3$; 200 MHz; delta): 5.874 (s broad; 2H; NH); 3.220–3.125 (m(dt and dq); 4H; N—CH$_2$); 1.460–1.320 (m(tt and tq); 4H; butyl-CH$_2$—CH$_2$); 1.112 (t; 3H; ethyl-CH$_3$; $J_E$=6.5 Hz); 0.858 (t; 3H; butyl-CH$_3$; $J_B$=6.5 Hz) ppm.

EXAMPLE 2

N-butyl-N'-propylurea was prepared in a yield of 78% of theory as described in Example 1, but using 2.46 g of propyl bromide as the alkylating agent.

$^1$H-NMR (CDCl$_3$; 200 MHz; delta): 5.864 and 5.836 (2t; each 1H; NH); 3.104 (2dt; each 2H; N—CH$_2$; $J_{CH2NH}$=6.0 Hz; $J_{CH2-CH2}$=7.4 Hz); 1.542–1.349 (m(tt and 2Tq); 6H; butyl-CH$_2$—CH$_2$ and propyl-CH$_2$); 0.906 (t; 6H; butyl-CH$_3$ and propyl-CH$_3$; J=7.3 Hz) ppm.

EXAMPLE 3

N-butyl-N'-ethylurea was obtained in the yield of 52% of theory as described in Example 1, but using 4.5 g of KOH pellets (80 mmol) and 0.55 g of potassium carbonate (4 mmol) as the bases and heating at reflux temperature for 16 hours. The $^1$H-NMR spectrum was entirely identical with that of Example 1.

EXAMPLE 4

N-butyl-N'-ethylurea was obtained in a yield of 80% of theory as described in Example 1, but using 1.54 g of diethyl sulfate (10 mmol) as the alkylating agent. The $^1$H-NMR spectrum was entirely identical with that of Example 1.

EXAMPLE 5

N-butyl-N'-ethylurea was obtained in a yield of 74% of theory as described in Example 1, but using 4.0 g of ethyl toluene-4-sulfonate (20 mmol) as the alkylating agent. The $^1$H-NMR spectrum was entirely identical with that of Example 1.

EXAMPLE 6

N-butyl-N'-ethylurea was obtained in a yield of 71% of theory as described in Example 1, but using 2.48 g of ethyl methanesulfonate (20 mmol) as the alkylating agent. The $^1$H-NMR spectrum was entirely identical with that of Example 1.

EXAMPLE 7

N-butyl-N'-ethylurea was obtained in a yield of 71% of theory as described in Example 1, but using 1.76 g of N-ethylurea (20 mmol) as the urea and 2.74 g of butyl bromide (20 mmol) as the alkylating agent. The $^1$H-NMR spectrum was entirely identical with that of Example 1.

Example 8

N-butyl-N'-isopropylurea was prepared in a yield of 58% as described in Example 1, but using 2.04 g of N-isopropylurea (20 mmol) as the urea and 2.74 g of butylbromide (20 mmol) as the alkylating agent.

$^1$H-NMR (CDCl$_3$; 200 MHz; delta): 5.708 (t; 1H; butyl-NH; $J_{CH2NH}$=5.5 Hz); 5.490 (d; 1H; isopropyl-NH; $J_{CHNH}$=7.9 Hz), 3.858 (dq; 1H; isopropyl-CH; $J_{CHNH}$=7.9 Hz; $J_{CHCH3}$=6.5 Hz); 3.135 (dse; 2H; butyl-N—CH$_2$; $J_{CH2NH}$=5.5 Hz; $J_{CH2CH2}$=6.7 Hz); 1.498–1.275 (m(tt and tq); 4H; butyl-CH$_2$—CH$_2$); 1.122 (d; 6H; isopropyl-CH$_3$; $J_{CHCH3}$=6.5 Hz); 0.906 (t; 3H; butyl-CH$_3$; $J_{CH2CH3}$=7.0 Hz) ppm.

EXAMPLE 9

N-butyl-N'-isopropylurea was prepared in a yield of 35% of theory as described in Example 1, but using 2.46 of 2-bromopropane (20 mmol) as the alkylating agent. The $^1$H-NMR spectrum was entirely identical with that of Example 8.

EXAMPLE 10

N,N'-dibutylurea was obtained in a yield of 82% of theory as described in Example 1, but using 2.74 g of butyl bromide (20 mmol) as the alkylating agent.

$^1$H-NMR (CDCl$_3$; 200 MHz; delta): 5.914 (t; 2H; NH; $J_{CH2NH}$=5.9 Hz); 3.135 (dt; 4H; N—CH$_2$; $J_{CH2NH}$=5.9 Hz; $J_{CH2CH2}$=6.7 Hz); 1.497–1.315 (m(tt and tq); 8H; butyl-CH$_2$—CH$_2$); 0.908 (t; 6H; CH$_3$); $J_{CH2CH3}$=7.0 Hz) ppm.

EXAMPLE 11

N,N'-dibutylurea was obtained in a yield of 75% of theory as described in Example 10, but using 4.5 g of KOH pellets (80 mmol) and 0.55 g of potassium carbonate (4 mmol) as the base and heating at reflux temperature for 12 hours. The $^1$H-NMR spectrum was entirely identical with that of Example 10.

EXAMPLE 12

N-N'-dibutylurea was obtained in a yield of 67% of theory as described in Example 1, but using 1.85 g of butyl chloride (20 mmol) as the alkylating agent and 4.5 g of KOH pellets (80 mmol) and 0.55 g of potassium carbonate (4 mmol) as the base and heating at reflux temperature for 12 hours. The $^1$H-NMR-spectrum was entirely identical with that of Example 10.

EXAMPLE 13

N-N'-dibutylurea was obtained in a yield of 21% of theory as described in Example 1, but using 1.85 g of butyl chloride (20 mmol) as the alkylating agent. The $^1$H-NMR spectrum was entirely identical with that of Example 10.

EXAMPLE 14

N-butyl-N'-tert.-butylurea was obtained in a yield of 47% of theory as described in Example 1, but using 2.32 g of tert.-butylurea (20 mmol) as the urea and 2.74 g of butyl bromide (20 mmol) as the alkylating agent.

$^1$H-NMR (CDCl$_3$; 200 MHz; delta): 5.421 (t; 1H; butyl-NH; $J_{CH2NH}$=6.0 Hz); 5.239 (s; 1H; tert.-butyl-NH); 3.093 (dt; 2H; N-CH$_2$; $J_{CH2NH}$=6.0 Hz; $J_{CH2CH2}$=6.3 Hz); 1.436–1.371 (m(tt and tq); 4H; butyl-CH$_2$—CH$_2$); 1.311 (s; 9H; tert.-butyl-CH$_3$); 0.896 (t; 3H; butyl-CH$_3$; $J_{CH2CH3}$=6.9 Hz) ppm.

EXAMPLE 15

After recrystallization from diethyl either, N-butyl-N'-decylurea was obtained in a yield of 96% of theory as described in Example 1, but using 4.47 g of decyl bromide (20 mmol) as the alkylating agent.

$^1$H-NMR (CDCl$_3$; 200 MHz; delta): 5.531 (t; 2H; NH; $J_{CH2NH}$=5.1 Hz); 3.161–3.072 (m(2dt); 4H; N—CH$_2$; $J_{CH2NH}$=5.1 Hz); 1.522–1.256 (M; 2OH; butyl- and decyl-CH$_2$); 0.941 (t; 3H; butyl-CH$_3$; $J_{CH2CH3(B)}$=6.0 Hz); 0.896 (t; 3H; decyl-CH$_3$; $J_{CH2CH3(D)}$=6.6 Hz) ppm.

EXAMPLE 16

N-butyl-N-'-decylurea was obtained in a yield of 95% of theory as described in Example 15, but using 3.54 g of decyl chloride (20 mmol) as the alkylating agent. The $^1$H-NMR spectrum was entirely identical with that of Example 15.

EXAMPLE 17

After recrystallization from n-hexane, N,N'-didecylurea was obtained in a yield of 97% of theory as described in Example 1, but using 4.0 of N-decylurea (20 mmol) and 4.47 g of decyl bromide.

$^1$H-NMR (CDCl$_3$; 200 MHz; delta): 4.524 (t; 2H, NH, $J_{CH_2NH}$=6.0 Hz); 3.139 (dt; 4H, N—CH$_2$; $J_{CH_2NH}$=6.0 Hz; $J_{CH_2CH_2}$=6.8 Hz); 1.481 (tt; 4H; N—CH$_2$—CH$_2$; $J_{CH_2CH_2}$=6.8 Hz); 1.259 (m; 32H; decyl-CH$_2$); 0.880 (t; 6H; CH$_3$, $J_{CH_2CH_3}$=6.5 Hz) ppm.

EXAMPLE 18

N-N'-didecylurea was obtained in a yield of 95% of theory as described in Example 17, but using 3.54 g of decyl chloride (20 mmol) as the alkylating agent. The $^1$H-NMR spectrum was entirely identical with that of Example 17.

EXAMPLE 19

N'-butylpyrrolidine-N-carboxamide was obtained in a yield of 41% of theory as described in Example 1, but using 2.28 of pyrrolidine carboxamide (20 mmol) as the urea and 2.74 g of butyl bromide (20 mmol) as the alkylating agent.

$^1$H-NMR (CDCl$_3$; 200 MHz; delta): 4.390 (t; 1H; NH; $J_{CH_2NH}$=5.8 Hz); 3.340 (t; 4H; N—CH$_2$; $J_{12}$=6.7 Hz); 3.222 (dt; 2H; HN—CH$_2$; $J_{CH_2NH}$=5.8 Hz; $J_{CH_2CH_2}$=7.0 Hz); 1.893 (tt; 4H; pyrrolidine-CH$_2$—CH$_2$; $J_{12}$=6.7 Hz; $J_{23}$=3.5 Hz); 1.536-1.288 (m(dt and tq); 4H; butyl-CH$_2$—CH$_2$); 0.921 (t; 3H; CH$_3$; $J_{CH_2CH_3}$=7.1 Hz) ppm.

EXAMPLE 20

N'-butylpyrrolidine-N-carboxamide was obtained in a yield of 70% of theory as described in Example 19, but using 4.5 g of KOH pellets (80 mmol) and 0.55 g of potassium carbonate (4 mmol) as the base and heating at reflux temperature for 16 hours. The $^1$H-NMR spectrum was entirely identical with that of Example 19.

EXAMPLE 21

N'-propylmorpholine-N-carboxamine was obtained in a yield of 60% of theory as described in Example 1, but using 2.60 g of morpholinecarboxamide (20 mmol) as the urea and 2.46 g of propyl bromide (20 mmol) as the alkylating agent.

$^1$H-NMR (CDCl$_3$; 200 MHz; delta): 4.992 (t; 1H; NH; $J_{CH_2NH}$=5.8 Hz); 3.634 (t; 4H; O—CH$_2$; J=5.0 Hz); 3.308 (t; 4H; N—CH$_2$; J=5.0 Hz); 3.132 (dt; 2H; HN—CH$_2$; $J_{CH_2NH}$=5.8 Hz; $J_{CH_2CH_2}$=7.3 Hz); 1.476 (tq; 2H; HN—CH$_2$—CH$_2$; $J_{CH_2CH_2}$=7.3 Hz; $J_{CH_2CH_3}$=7.3 Hz); 0.870 (t; 3H; CH$_3$; $J_{CH_2CH_3}$=7.3 Hz) ppm.

EXAMPLE 22

N'-isopropylmorpholine-N-carboxamide was obtained in a yield of 26% of theory as described in Example 21, but using 2.46 g of 2-bromopropane.

$^1$NMR(CDCl$_3$; 200 MHz; delta): 4.555 (d; 1H; NH; $J_{CHNH}$=6.7 Hz); 3.969 (dse; 1H; HN—CH; $J_{CHNH}$=6.7 Hz; $J_{CHCH_3}$=6.6 Hz); 3.675 (t; 4H, O—CH$_2$; J=4.9 Hz); 3.328 (t; 4H; N—CH$_2$; J=4.9 Hz); 1.153 (d; 6H; CH$_3$; $J_{CHCH_3}$6.6 Hz) ppm.

EXAMPLE 23

N'-butylmorpholine-N-carboxamide was obtained in a yield of 85% of theory as described in Example 21, but using 2.74 g of butyl bromide (20 mmol) as the alkylating agent.

$^1$H-NMR (CDCl$_3$; 200 MHz; delta): 5.413 (t; 1H; NH; $J_{CH_2NH}$=6.0 Hz); 3.664 (t; 4H; O—CH$_2$; J=5.0 Hz); 3.360 (t; 4; N—CH$_2$; J=5.0 Hz); 3.190 (dt; 2H; HN—CH$_2$; $J_{CH_2NH}$=6.0 Hz; $J_{CH_2CH_2}$=6.7 Hz); 1.522-1.275 (m(tt and tq); 4H; butyl-CH$_2$—CH$_2$); 0.917 (t; 3H; CH$_3$; $J_{CH_2CH_3}$=6.7 Hz) ppm.

EXAMPLE 24

After recrystallization from n-hexane, N'-decylmorpholine-N-carboxamide was obtained in a yield of 88% of theory as described in Example 21, but using 4.47 g of decylbromide (20 mmol).

$^1$-NMR (CDCl$_3$; 200 MHz; delta); 4.787 (t; 1H; NH; $J_{CH_2NH}$=5.6 Hz); 3.678 (t; 4H; O—CH$_2$; J=5.0 Hz); 3.340 (t; 4H; N—CH$_2$; J=5.0 Hz); 3.208 (dt; 2H; HN—CH$_2$; $J_{CH_2NH}$=5.6 Hz; $J_{CH_2CH_2}$=7.2 Hz); 1.493 (tt; 2H; HN—CH$_2$—CH$_2$; $J_{CH_2CH_2}$= 7.2 Hz); 1.261 (m; 14H; decyl-CH$_2$); 0.880 (t; 3H, CH$_3$, $J_{CH_2CH_3}$=6.5 Hz) ppm.

EXAMPLE 25

2.25 g of powdered KOH (40 mmol) were suspended under argon in 20 ml of anhydrous dimethyl sulfoxide. After 10 minutes 0.6 g of urea (10 mmol) and 2.12 g of hexyl iodide (10 mmol) were added with vigorous stirring, and the mixture were stirred for a further 30 minutes at room temperature. When the reaction was complete, the reaction mixture was poured into 150 ml of distilled water, and the resulting suspension was extracted with methylene chloride and chloroform. The organic phase was washed with water, dried over sodium sulfate and evaporated. This gave 0.33 g of N-hexylurea, i.e. 26% of theory.

$^1$H-NMR (CDCl$_3$; 200 MHz; delta): 5.895 (t; 1H; NH; $J_{CH_2NH}$=5.3 Hz); 5.359 (s; 2H, NH$_2$); 2.914 (dt; 2H; N—CH$_2$; $J_{CH_2NH}$=5.3 Hz; $J_{CH_2CH_2}$=6.4 Hz); 1.312-1.230 (m; 8H; hexyl-CH$_2$); 0.846 (t; 3H; CH$_3$; J=6.5 Hz) ppm.

EXAMPLE 26

N,N'-dibutylurea was obtained in the yield of 22% of theory as described in Example 25, but using 1.16 g of butylurea (10 mmol) as the urea and 1.37 g of butyl bromide (10 mmol) as the alkylating agent. The $^1$H-NMR spectrum was entirely identical with that of Example 10.

What we claim is:
1. Process for the preparation of ureas of the formula

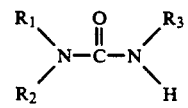

I in which R$_1$ and R$_2$ independently of one another denote hydrogen, a linear, branched or cyclic alkyl group which is unsubstituted or substituted by groups inert under the conditions of the reaction, or an aralkyl group, or $R_1$ and $R_2$, together with the nitrogen atom, denote a non-aromatic, heterocyclic ring and $R_3$ denotes an alkyl group which is unsubstituted or substituted by groups inert under the conditions of the reaction, the tertiary butyl group being excluded, comprising N-alkylating a urea of the formula

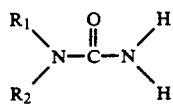    II in which $R_1$ and $R_2$ have the abovementioned meaning in the presence of a solid base and in the presence of a phase transfer catalyst in a diluent at temperature of 0° to 150° C. with an alkylating agent of the formula

    III in which $R_3$ has the meaning indicated above and n denotes the numbers 1 or 2, X representing a sulfonic acid or bisulfate group in the event that n denotes the number 1, and X representing a sulfate group in the event than n denotes the number 2.

2. Process according to claim 1, comprising employing
a urea of the formula II in which $R_1$ and $R_2$ independently of one another denote hydrogen or an unsubstituted, linear or branched alkyl group having 2 to 18 C atoms, or $R_1$ and $R_2$, together with the nitrogen atom, denote a pyrrolidine, piperidine or morpholine ring.

3. Process according to claim 1 comprising employing as base a solid alkali metal hydroxide with or without the addition of 2 to 20 mol % of a solid alkali metal carbonate, relative to the alkali metal hydroxide.

4. Process according to claim 1 comprising employing 1.5 to 8 mol of the solid base per mole of urea of the formula II.

5. Process according to claim 1 comprising employing a quaternary ammonium salt as the phase transfer catalyst.

6. Process according to claim 1 comprising employing an aromatic hydrocarbon as the diluent.

7. Process according to claim 1 comprising employing dimethyl sulfoxide as the diluent and as the catalyst.

8. Process according to claim 1 comprising carrying out the reaction at the reflux temperature of the diluent, unless dimethyl sulfoxide is employed as the diluent.

9. Process according to claim 1 comprising employing an alkylating agent of the formula III in which $R_3$ denotes a linear or branched, unsubstituted alkyl group and X denotes a 4-toluenesulfonate, methylsulfonate or sulfate group.

10. Process according to claim 1 comprising employing the urea of the formula II and the alkylating agent of the formula III in an equimolar ratio.

* * * * *